United States Patent
Mitsuhashi

(10) Patent No.: US 10,264,979 B2
(45) Date of Patent: Apr. 23, 2019

(54) OBJECT INFORMATION OBTAINING SYSTEM, SIGNAL PROCESSING METHOD, AND NON-TRANSITORY STORAGE MEDIUM

(71) Applicant: CANON KABUSHIKI KAISHA, Tokyo (JP)

(72) Inventor: Kenji Mitsuhashi, Saint Louis, MO (US)

(73) Assignee: CANON KABUSHIKI KAISHA, Tokyo (JP)

( * ) Notice: Subject to any disclaimer, the term of this patent is extended or adjusted under 35 U.S.C. 154(b) by 357 days.

(21) Appl. No.: 14/311,613

(22) Filed: Jun. 23, 2014

(65) Prior Publication Data

US 2015/0005611 A1    Jan. 1, 2015

(30) Foreign Application Priority Data

Jun. 26, 2013  (JP) .................. 2013-133533

(51) Int. Cl.
*A61B 5/00* (2006.01)
*A61B 8/00* (2006.01)
(Continued)

(52) U.S. Cl.
CPC .......... *A61B 5/0095* (2013.01); *A61B 5/7203* (2013.01); *A61B 5/7228* (2013.01);
(Continued)

(58) Field of Classification Search
None
See application file for complete search history.

(56) References Cited

U.S. PATENT DOCUMENTS 4,549,289 A * 10/1985 Schwartz .................. G01H 7/00
                                                            369/53.1
4,640,132 A *  2/1987 Flora ........................ G01N 29/07
                                                            73/602
(Continued)

FOREIGN PATENT DOCUMENTS

CN          101039626 A      9/2007
CN          101849840 A     10/2010
(Continued)

OTHER PUBLICATIONS

Pai-Chi Li et al.; "Adaptive Imaging Using the Generalized Coherence Factor;" IEEE Transactions on Ultrasonics, Ferroelectrics, and Frequency Control, vol. 50, No. 2, Feb. 2003, pp. 128-141.*
(Continued)

*Primary Examiner* — Tse W Chen
*Assistant Examiner* — Jason M Ip
(74) *Attorney, Agent, or Firm* — Canon U.S.A., Inc. IP Division

(57) ABSTRACT

An object information obtaining system disclosed herein includes a holding member that holds an object; a probe that detects acoustic waves at a plurality of positions and obtains a plurality of time-series detection signals, the acoustic waves having occurred inside the object and having propagated through the holding member; and a signal processor that obtains a first frequency signal on the basis of the plurality of time-series detection signals, that obtains a second frequency signal, in which phase modulation is corrected, by performing, on the first frequency signal, correction of phase modulation of the acoustic waves due to the holding member, and that obtains object information inside the object on the basis of the second frequency signal, in which the phase modulation is corrected.

30 Claims, 9 Drawing Sheets

(51) Int. Cl.
*A61B 8/08* (2006.01)
*G01S 7/52* (2006.01)
(52) U.S. Cl.
CPC ............ *A61B 5/742* (2013.01); *A61B 8/4209* (2013.01); *A61B 8/429* (2013.01); *A61B 8/5207* (2013.01); *A61B 8/5269* (2013.01); *G01S 7/52049* (2013.01); *A61B 8/0825* (2013.01); *A61B 8/403* (2013.01)

(56) References Cited

U.S. PATENT DOCUMENTS

| | | | |
|---|---|---|---|
| 5,675,550 | A | 10/1997 | Ekhaus |
| 7,505,135 | B2 * | 3/2009 | Granot ................. A61B 5/0059 356/432 |
| 2004/0006272 | A1 | 1/2004 | Vortman |
| 2011/0182136 | A1 * | 7/2011 | Tanji .................... A61B 5/0059 367/7 |
| 2011/0251475 | A1 * | 10/2011 | Tokita .................. A61B 5/0091 600/407 |

FOREIGN PATENT DOCUMENTS

| | | | | |
|---|---|---|---|---|
| EP | 2287632 | * | 7/2005 | ............... G01S 7/52 |
| EP | 2287632 A1 | | 2/2011 | |
| JP | H05-063509 U | | 8/1993 | |
| JP | H11-216143 A | | 8/1999 | |
| JP | 2010-167258 A | | 8/2010 | |
| JP | 2011-172611 A | | 9/2011 | |

OTHER PUBLICATIONS

Treeby et al.; "k-Wave: MATLAB toolbox for the simulation and reconstruction of photoacoustic wave fields;" Journal of Biomedical Optics; 15(2), 021314. Mar./Apr. 2010.*
Pai-Chi-Li et al.; "Adaptive Imaging Using the Generalized Coherence Factor;" IEEE Transactions on Ultrasonics, Ferroelectrics, and Frequency Control, vol. 50, No. 2, Feb. 2003, pp. 128-141; XP011368416.

* cited by examiner 50 mm

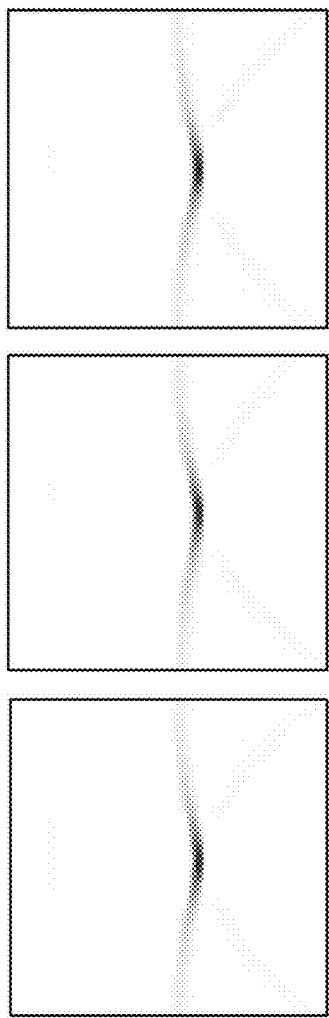
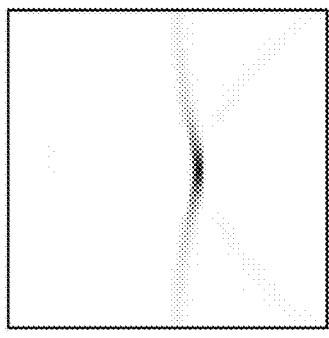
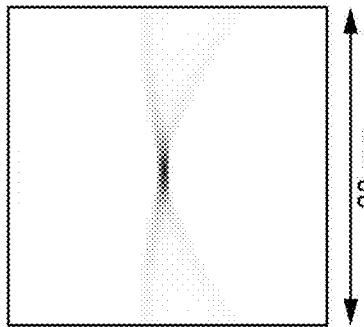
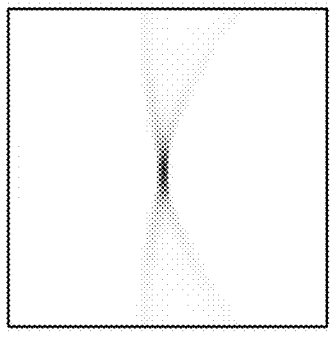
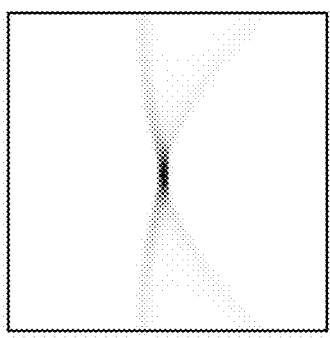
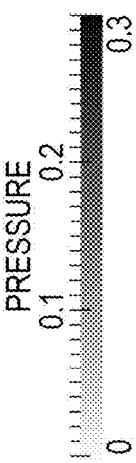

OBJECT INFORMATION OBTAINING SYSTEM, SIGNAL PROCESSING METHOD, AND NON-TRANSITORY STORAGE MEDIUM

BACKGROUND OF THE INVENTION

Field of the Invention

The present invention relates to an object information obtaining system, a signal processing method, and a non-transitory storage medium.

Description of the Related Art

Object information obtaining systems such as photoacoustic imaging apparatuses or ultrasonic echo imaging apparatuses have been developed thus far as technologies for obtaining information inside an object, such as a living body, by detecting acoustic waves.

In the case, however, where the sound velocity of acoustic waves that propagate through media from an acoustic wave source to a probe is not constant, the acoustic waves are refracted. Detection signals of the refracted acoustic waves provide a low quantitativeness of object information. When the object information is converted into an image, the image consequently has distortion or a low contrast.

In order to minimize the above-described reduction of the quantitativeness of object information, the effect of the non-uniformity of the sound velocity has to be minimized. In the imaging technology using acoustic waves, the following method is included as an example of a method for reducing the effect of the non-uniformity of the sound velocity.

Japanese Patent Laid-Open No. 2010-167258 discloses a method for correcting the effect of refraction by tracing the propagation paths of acoustic waves in accordance with the Snell's law and calculating the arrival time from the propagation distance of the acoustic waves.

The method described in Japanese Patent Laid-Open No. 2010-167258 involves tracing of the propagation paths of multiple sound rays of acoustic waves, which have occurred as spherical waves, in accordance with the Snell's law and thus requires a large number of calculations. Consequently, the method described in Japanese Patent Laid-Open No. 2010-167258 is unsuitable for accelerating the calculations for correcting the effect of refraction.

SUMMARY OF THE INVENTION

The present invention was made in view of the above-described scenarios. The present invention provides an object information obtaining system that can reduce the effect of the non-uniformity of the sound velocity with a small calculation amount.

An object information obtaining system disclosed herein includes a holding member that holds an object; a probe that detects acoustic waves at a plurality of positions and obtains a plurality of time-series detection signals, the acoustic waves having occurred inside the object and having propagated through the holding member; and a signal processor that obtains a first frequency signal on the basis of the plurality of time-series detection signals, that obtains a second frequency signal, in which phase modulation is corrected, by performing, on the first frequency signal, correction of phase modulation of the acoustic waves due to the holding member, and that obtains object information inside the object on the basis of the second frequency signal, in which the phase modulation is corrected. Further features of the present invention will become apparent from the following description of exemplary embodiments (with reference to the attached drawings).

BRIEF DESCRIPTION OF THE DRAWINGS

FIGS. 9A to 9G illustrate results of the correction of the phase modulation and results of the correction of the wave number modulation according to examples.

DESCRIPTION OF THE EMBODIMENTS

First Embodiment

Figure 1:
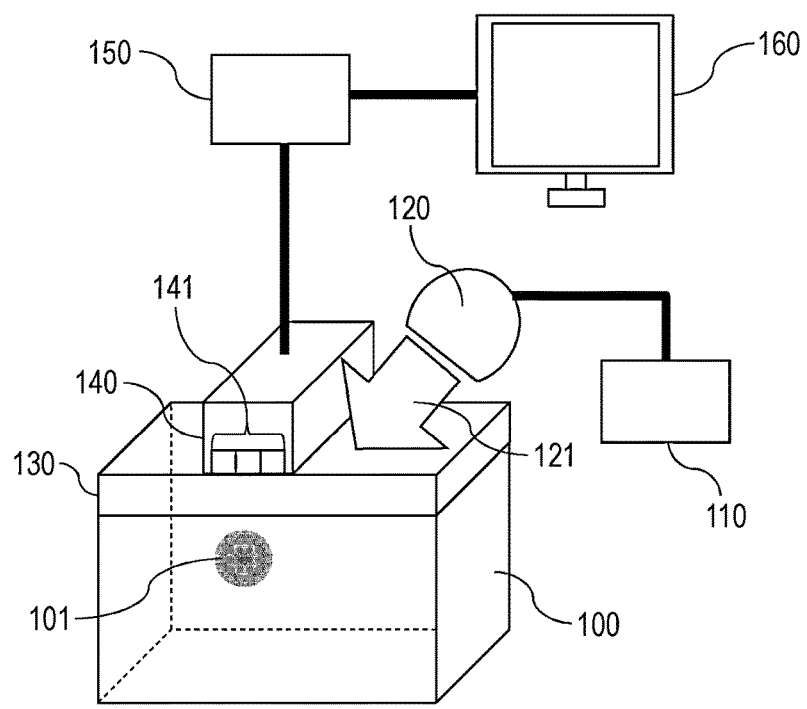
FIG. 1 schematically illustrates an object information obtaining system according to an embodiment.

A first embodiment describes a photoacoustic system, which is an example of an object information obtaining system, in detail below referring to the drawings. The photoacoustic system is a system that obtains object information from detection signals of photoacoustic waves that have occurred due to a photoacoustic effect. Examples of the object information obtainable from detection signals of photoacoustic waves include the initial acoustic pressure of photoacoustic waves, the light energy absorbance of photoacoustic waves, the absorption coefficient of photoacoustic waves, and the concentration of materials constituting the object. Here, examples of the concentration of materials include an oxygen saturation, an oxyhemoglobin concentration, a deoxyhemoglobin concentration, and a total hemoglobin concentration. The total hemoglobin concentration is the sum of the oxyhemoglobin concentration and the deoxyhemoglobin concentration. In this embodiment, the object information does not have to be numerical data and may be information of distribution of positions inside the object. In other words, the object information may also include distribution information such as the distribution of the absorption coefficient or the distribution of the oxygen saturation.

The present invention is applicable to not only a photoacoustic system but also an acoustic-wave echo device that obtains object information by detecting echoes of the acoustic waves. Examples of the object information obtainable from detection signals of echoes of acoustic waves include a brightness mode (B-mode) image that represents the distribution of the strength of echoes of acoustic waves. In addition, examples of the object information may include a Doppler-mode image, which represents the velocity distribution of a structure in the object, an elastography image, which represents the elasticity distribution (distortion factor, distortional wave velocity, or Young's modulus) in the structure of the object, and speckle pattern data attributable to scattering of acoustic waves inside the object.

Configuration of Object Information Obtaining System

FIG. 1 schematically illustrates an object information obtaining system according to the embodiment. Now, components of the system will be described.

The object information obtaining system according to the embodiment includes a light source 110, an optical system 120, a holding member 130, a probe 140 including multiple transducers 141, a signal processor 150 serving as a computer, and a display unit 160.

Figure 2:
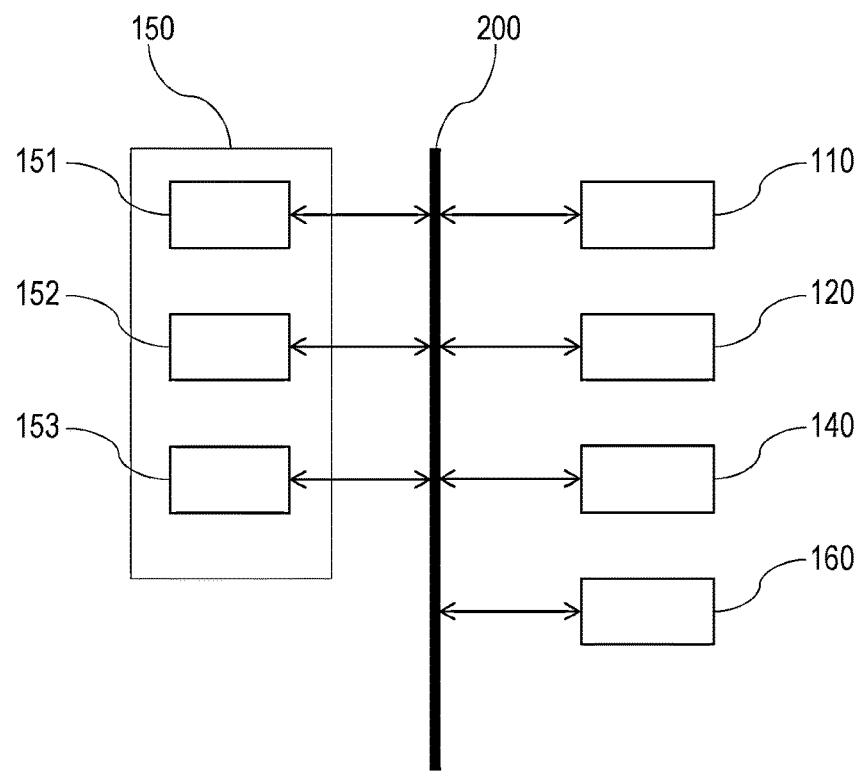
FIG. 2 illustrates the details of a signal processor according to an embodiment and components around the signal processor.

FIG. 2 schematically illustrates the details of the signal processor 150 and components around the signal processor 150. As illustrated in FIG. 2, the signal processor 150 includes a controller 151, a computation unit 152, and a memory unit 153.

The controller 151 controls operations of the components constituting the object information obtaining system via a bus 200. The controller 151 also reads a program that describes a method for obtaining object information, which will be described below, stored in the memory unit 153, so that the object information obtaining system executes the method for obtaining object information.

The holding member 130 disposed between the object 100 and the probe 140 holds an object 100. When a light beam produced by the light source 110 is projected on the object 100 as a pulse light beam 121 via the optical system 120, acoustic waves (photoacoustic waves) occur inside the object 100 due to the photoacoustic effect. The probe 140 detects the acoustic waves that have propagated through the holding member 130 and obtains time-series electric signals. The signal processor 150 obtains object information on the basis of the time-series electric signals and causes the display unit 160 to display the object information.

In the case where an interface between two layers, such as the object 100 and the holding member 130 in which acoustic waves travel at different velocities, exists, the acoustic waves are refracted at the interface. This refraction changes the phase of the acoustic waves detected by the probe 140 from the phase of the acoustic waves that would be detected by the probe 140 in the case where the holding member 130 is not provided. In other words, unless the phase modulation is corrected, the obtainable quantitativeness of object information will decrease. The object information obtaining system according to the embodiment can minimize the decrease of an obtainable quantitativeness of object information by correcting the phase modulation of acoustic waves.

Hereinbelow, the components of the object information obtaining system according to the embodiment will be described in detail.

Object 100 and Light Absorber 101

Although an object 100 and a light absorber 101 do not constitute the object information obtaining system according to the invention, the object 100 and the light absorber 101 are described as follows. The object information obtaining system of the present invention is mainly used to diagnose human or animal disorders, such as malignant tumors or vascular diseases, follow up chemotherapy, or perform other operations. Thus, intended objects are living bodies, specifically, parts to be examined such as the human or animal breast, neck, or abdomen.

An intended light absorber inside the object is a part that has a relatively high light absorption coefficient inside the object. For example, in the case where the human body is an object of examination, oxyhemoglobin, deoxyhemoglobin, blood vessels conveying a large number of oxyhemoglobin or deoxyhemoglobin, or malignant tumors containing a large number of new blood vessels can serve as light absorbers. In addition, plaques on the carotid wall or other objects also can serve as a light absorber.

Light Source 110

The light source 110 may be a pulse light source that can produce pulse light beams of the order of several nanoseconds to several microseconds. Specifically, in order to efficiently produce photoacoustic waves, the light source 110 may be capable of producing light beams having a pulse width of the order of ten nanoseconds. The light source 110 may be capable of producing light beams of such a wavelength that the light beams can propagate into the object. Specifically, in the case where the living body is used as an object, the wavelength suitable for the living body falls within 500 nm to 1200 nm. However, in the case where the distribution of the optical characteristics of a tissue of the living body relatively close to the surface of the living body is obtained, the wavelength range ranging, for example, from 400 nm to 1600 nm, which is wider than the above-described wavelength range, may be used.

A laser or a light emitting diode may be used as a light source. Examples of the laser include a solid laser, a gas laser, a dye laser, and a semiconductor laser. For example, lasers used in this embodiment include an alexandrite laser, an yttrium-aluminum-garnet laser, and a titan-sapphire laser.

Optical System 120

Light beams emitted from the light source 110 are guided to the object 100 while being shaped into a desired shape of light distribution by typical optical components such as a lens and a mirror. Instead, the light beams may propagate through optical waveguides such as optical fibers. Examples of the optical components include a mirror that reflects light beams, a lens that concentrates or expands light beams or changes the shape of light beams, a prism that disperses, refracts, or reflects light beams, an optical fiber that propagates light beams, and a diffusion sheet that diffuses light beams. Optical components may be any components as long as they are used to project light beams emitted from the light source 110 on the object in a desired shape.

In the case where the light source 110 can emit light beams and guide the light beams to the object in a desired shape, the optical system 120 may be omitted.

Holding Member 130

The holding member 130 is a member that holds the object 100.

The holding member 130 is not limited to a parallel plate illustrated in the embodiment and may have any shape, such as a hemisphere, as long as the member 130 can hold the object 100. Alternatively, two parallel plates may be provided as holding members to hold the object 100 by sandwiching the object 100 therebetween.

The holding member 130 may be a film form member. Specifically, the holding member 130 may be made of a material that is softer than the object 100 such as the breast.

The holding member 130 may be made of a material that acoustically matches the probe 140 to a high degree. In the case where pulse light beams are projected on the object 100 through the holding member 130, the holding member 130 may be made of a material having a high transmissivity of pulse light beams. Examples of the material of the holding member 130 include plastics such as polymethylpentene or acrylic resin and glass.

In the case where the object 100 does not have to be held, the object information obtaining system does not have to include the holding member 130.

Probe 140

The probe 140 includes transducers, which are elements that can detect acoustic waves, and a housing that surrounds the transducers.

The transducers detect acoustic waves such as photoacoustic waves and ultrasonic echoes and convert the acoustic waves into electric signals, which are analogue signals. The transducers may be any transducers that can detect acoustic waves using, for example, the piezoelectricity, optical resonance, or change in capacitance.

Typical photoacoustic waves are acoustic waves of 100 kHz to 100 MHz. Thus, in the case of detecting photoacoustic waves, transducers that can detect acoustic waves having frequencies within the above range are suitably used. In the case of detecting echoes of acoustic waves transmitted by an acoustic-wave echo device, transducers that match the frequency of the transmitted acoustic waves are suitably used. Typical acoustic-wave echo devices transmit and receive acoustic waves of 1 MHz to 1000 MHz.

In the embodiment, the probe 140 may include multiple transducers arranged in an array with there being the need for detecting acoustic waves at multiple positions. The multiple transducers may be arranged in a line or on a plane. Here, the arrangement in a line or on a plane includes an arrangement in substantially a line or on substantially a plane. In other words, even in the case where the multiple transducers are arranged in a curved shape, if the radius of curvature of the curve is sufficiently large with respect to the distance (pitch) between detecting elements, the present invention is applicable to such a configuration. For example, in the case where the radius of curvature is ten times the pitch or larger, the present invention is applicable to such a configuration.

An acoustic-wave detection surface according to the embodiment refers to the surface on which detection surfaces of the multiple transducers 141 are arranged.

Signal Processor 150

As illustrated in FIG. 2, the signal processor 150 includes a controller 151, a computation unit 152, and a memory unit 153.

An element such as a central processing unit (CPU) is typically used as the controller 151.

An element such as a CPU, a graphics processing unit (GPU), or an analog-to-digital (A/D) converter or a circuit such as a field-programmable gate array (FPGA) or an application specific integrated circuit (ASIC) is typically used as the computation unit 152. The computation unit 152 may be constituted by more than one element and/or circuit. Any of the elements and the circuits may execute each operation involved in the method for obtaining object information. A device that executes each operation is collectively referred to as a computation unit according to the embodiment.

A storage medium such as a read-only memory (ROM), a random access memory (RAM), or a hard disk is typically used as the memory unit 153. The memory unit 153 may be constituted by more than one storage medium.

The signal processor 150 may be capable of simultaneously performing pipeline processing of multiple signals. Such a signal processor can minimize the time taken for obtaining object information.

Operations involved in the method for obtaining object information may be stored in the memory unit 153 in the form of a program that is to be executed by the computation unit 152. Here, the memory unit 153 in which the program is stored is a non-transitory storage medium.

The signal processor and the multiple transducers may be integrated together in a common housing. Here, the signal processor in the housing may perform part of signal processing and another signal processor disposed outside the housing may perform the remaining part of signal processing. In this case, the signal processors disposed inside and outside the housing may be collectively referred to as a signal processor according to the embodiment.

Display Unit 160

The display unit 160 is a device that displays object information output from the signal processor 150. A liquid crystal display or the like is typically used as the display unit 160. Alternatively, another type of a display such as a plasma display, an organic electroluminescent display, or a field emission display (FED) may be used.

The display unit 160 may be provided separately from the object information obtaining system according to the embodiment.

Method for Obtaining Object Information

Figure 3:
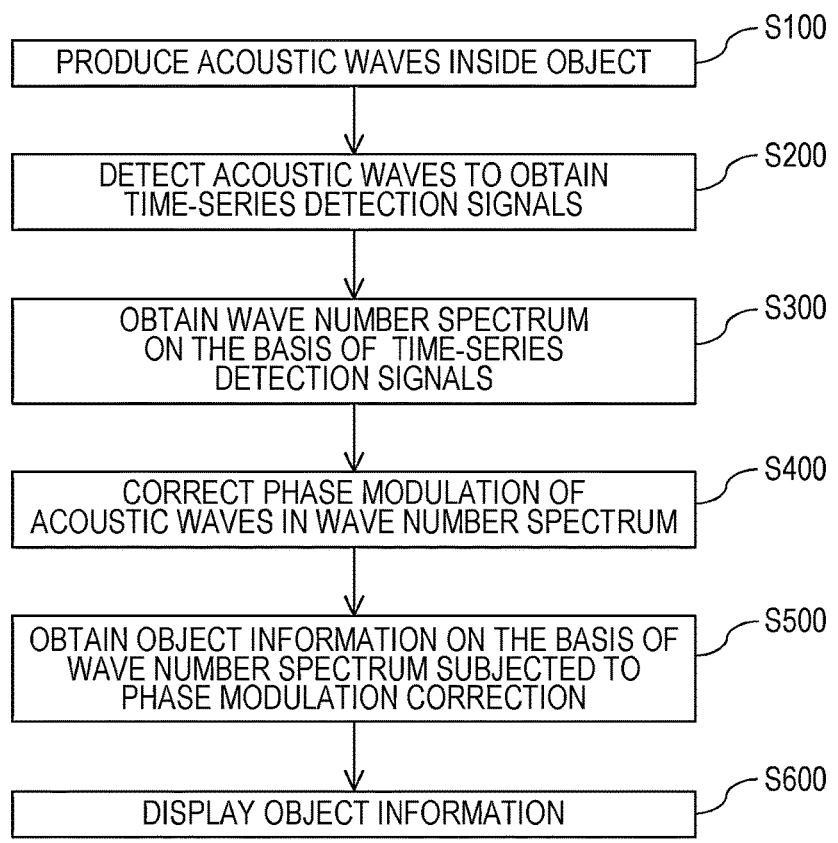
FIG. 3 is a flow chart of a method for obtaining object information according to a first embodiment.

Referring now to FIG. 3, steps of the method for obtaining object information according to the embodiment will be described. The steps are executed as a result of the controller 151 controlling the operation of each component of the object information obtaining system. Specifically, the method for operating the object information obtaining system according to the embodiment will be described as below.

S100: Step of Producing Acoustic Waves Inside Object

Light beams produced by the light source 110 are projected on the object 100 as pulse light beams 121 via the optical system 120. The object 100 then absorbs the pulse light beams 121, whereby acoustic waves (photoacoustic waves) occur due to the photoacoustic effect.

Here, acoustic waves may be transmitted to the object 100 and echoes that have occurred as a result of the transmitted acoustic waves reflecting inside the object 100 may be used as acoustic waves in the invention. In this case, the object information obtaining system has to include an acoustic wave transmitter that transmits acoustic waves. To this end, the multiple transducers 141 may be used not only as an acoustic wave detector but also as an acoustic wave transmitter. In other words, an acoustic wave detector and an acoustic wave transmitter may be formed by one transducer array.

S200: Step of Detecting Acoustic Waves to Obtain Time-Series Detection Signals

In this step, the probe 140 detects acoustic waves that have propagated through the holding member 130 and outputs multiple time-series detection signals $p_d(x, y, t)$. The output time-series detection signals are stored in the memory unit 153.

Here, the time-series detection signals represent actual measured values of the pressure of the acoustic waves. The obtained multiple time-series detection signals according to the embodiment have to determine one pressure value in relation to the space coordinate and the time coordinate. To this end, the probe 140 according to this embodiment includes the multiple transducers 141 so that acoustic waves can be detected as time-series signals at multiple positions. In addition, in order to detect acoustic waves at multiple positions, the object information obtaining system may include a scanner (not illustrated) that scans the probe.

Here, the space coordinate is a coordinate that indicates the position at which measurement is done. In other words, in the embodiment, the space coordinate is a position coordinate of each transducer. In addition, the time coordinate is a coordinate that indicates the time at which each transducer detects an acoustic wave.

S300: Step of Performing Fourier Transform on Time-Series Detection Signals to Obtain Wave Number Spectrum In this step, the computation unit 152 performs the Fourier transform on multiple time-series detection signals in a spatial direction (direction in which the space coordinate extends) and in a time direction (direction in which the time coordinate extends) to obtain a frequency spectrum $K_f(k_{x1}, k_{y1}, \omega)$ and stores the frequency spectrum $K_f$ in the memory unit 153.

For example, on the basis of Journal of Biomedical Optics 15 (2), 021314 (March/April 2010)), the computation unit 152 performs the Fourier transform on time-series detection signals $p_d$ in accordance with Expression 1 to obtain the frequency spectrum $K_f$ as frequency signals including a time frequency.

$$K_f(k_x, k_y, \omega) = \frac{c_0^2 k_{z1}}{2\omega} F_{x,y,t}\{p_d(x, y, t)\}$$ (Expression 1)

In Expression 1, $k_x$, $k_y$, and $k_z$ denote wave numbers (also called spatial frequencies) (1/m) in the directions of x, y, and z axes, respectively. Generally, a wave number is a quantity obtained by multiplying a spatial frequency by $2\pi$ (rad) and expressed in the unit of rad/m. In this invention, the spatial frequency is referred to as a wave number for convenience's sake. In addition, $\omega$ denotes a time frequency (1/s), $c_0$ denotes the sound velocity inside the object, and $F_{x, y, t}$ denotes the Fourier transform.

In this embodiment, acoustic waves are detected by the detection surfaces of the multiple transducers 141 arranged in a (x, y) plane. Thus, the frequency spectrum obtained by the Fourier transform is expressed as a function of the wave numbers in the x and y axis directions and the time frequency $\omega$.

The frequency spectrum is obtained as a set of complex numbers obtained when $k_x$, $k_y$, and $\omega$ take specific values. In other words, a complex number corresponding to each combination of $k_x$, $k_y$, and $\omega$ is stored in the memory unit 153.

Typically, the numbers of $k_x$ and $k_y$ are determined on the basis of the number of transducers 141 and the number of time frequency $\omega$ is determined on the basis of the number of time-series detection signals sampled in the time direction. The upper limits of the numbers of $k_x$ and $k_y$ and the frequency $\omega$ may be changed by interpolation of multiple signals. Alternatively, the numbers $k_x$ and $k_y$ and the frequency $\omega$ may be increased or reduced by adding zero (zero padding) to the signals or deleting some signals.

Subsequently, on the basis of Journal of Biomedical Optics 15 (2), 021314 (March/April 2010)), the computation unit 152 converts the time frequency $\omega$ of the frequency spectrum stored in the memory unit 153 in accordance with Expression 2 into a wave number $k_z$ in the z axis direction and obtains a wave number spectrum $K(k_y, k_y, k_z)$ of a frequency signal expressed only by wave numbers. The complex numbers of the obtained wave number spectrum ($k_x$, $k_y$, $k_z$) are stored in the memory unit 153 as measured values.

$$k_z = \sqrt{(\omega/c)^2 - k_x^2 - k_y^2}$$ (Expression 2)

In this embodiment, a spectrum including the time frequency is referred to as a frequency spectrum and the spectrum obtained after converting the time frequency into a wave number is referred to as a wave number spectrum.

The computation unit 152 may obtain the wave number spectrum on the basis of the time-series detection signals without obtaining the frequency spectrum. In other words, the computation unit 152 may obtain the wave number spectrum on the basis of the time-series detection signals using an expression obtained by substituting Expression 2 into Expression 1.

Alternatively, the Fourier transform in this step may be performed by the fast Fourier transform for reduction of calculations.

Hereinbelow, a combination ($k_x$, $k_y$, and $k_z$) of the spatial frequencies is simply referred to as a "wave number". In this embodiment, signals in a frequency space are collectively referred to as a frequency signal. In this embodiment, the computation unit obtains the frequency spectrum or the wave number spectrum, as the first frequency signal, based on the multiple time-series detection signals.

S400: Step of Performing Correction of Phase Modulation of Acoustic Waves on Wave Number Spectrum In this step, the computation unit 152 performs correction of phase modulation of acoustic waves on the wave number spectrum stored in the memory unit 153, the phase modulation being attributable to refraction of the acoustic waves at the holding member 130. That is, the computation unit 152 obtains a second frequency signal in which phase modulation is corrected.

Figure 4:
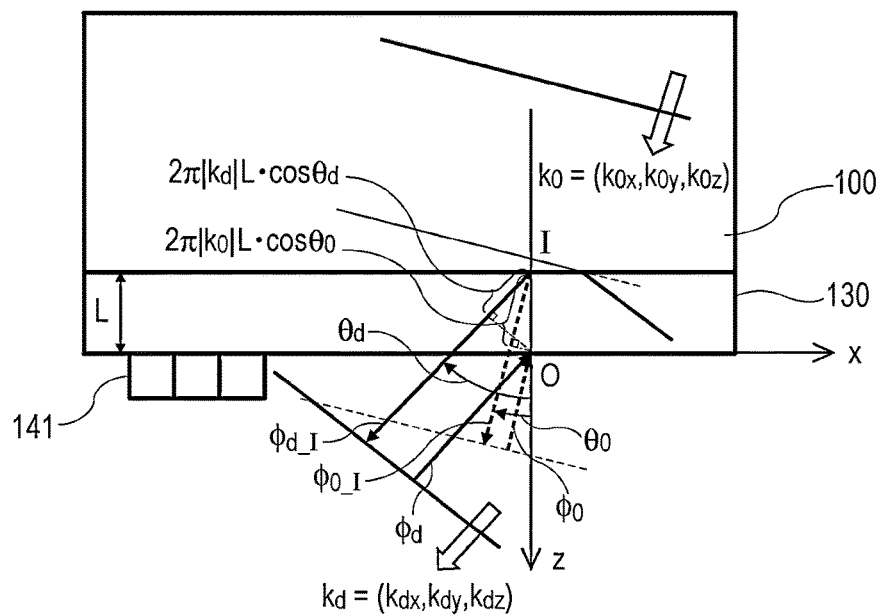
FIG. 4 illustrates correction of phase modulation according to the first embodiment.

Referring now to FIG. 4, a method for correcting the phase modulation of the measured value $K_d$ corresponding to the wave number $k_d = (k_{dx}, k_{dy}, k_{dz})$ in the wave number spectrum, which is a set of measured values (complex numbers) corresponding to the multiple wave numbers, is described. The wave number $k_d = (k_{dx}, k_{dy}, k_{dz})$ is a wave number of acoustic waves that have propagated through the holding member 130 and detected by the multiple transducers 141. Here, the wave number of the acoustic waves that have not yet propagated through the holding member 130 is assumed as $k_0 = (k_{0x}, k_{0y}, k_{0z})$. In step S300, the case where the Fourier transform is performed with respect to the origin O is assumed. The origin O may be determined at any position on the acoustic-wave detection surface (x, y).

In this embodiment, acoustic waves are refracted at the interface between the object 100 and the holding member 130. FIG. 4 illustrates propagation of the acoustic waves with an illustration of the peak of the amplitude of the acoustic waves. In FIG. 4, solid lines indicate the state where acoustic waves that have occurred in the object 100 are refracted and propagate through the holding member 130. On the other hand, dotted lines indicate the state where hypothetic acoustic waves that are not refracted propagate.

In addition, $\theta_0$ denotes an incidence angle of the acoustic waves that enter the holding member 130 from the object 100 and $\theta_d$ denotes a refraction angle of the acoustic waves that have been refracted at the interface between the object 100 and the holding member 130.

Firstly, the computation unit 152 obtains the incidence angle $\theta_0$ and the refraction angle $\theta_d$.

Here, when the wave number $k_d$ is determined, the direction in which the acoustic waves propagate through the holding member 130 is determined. Thus, $\theta_d$ is also uniquely determined. In accordance with the Snell's law ($\sin \theta_0/\sin \theta_d = c_0/c_1$), $\theta_0$ is uniquely determined on the basis of $\theta_d$, the sound velocity $c_0$ inside the object 100, and the sound velocity $c_1$ inside the holding member 130. In other words, when the sound velocity $c_0$ inside the object 100 and the sound velocity $c_1$ inside the holding member 130 have been found in advance, $\theta_d$ and $\theta_0$ corresponding to the wave number $k_d$ are uniquely determined.

Thus, the computation unit 152 can calculate the incidence angle $\theta_0$ and the refraction angle $\theta_d$ in accordance with the Snell's law on the basis of the wave number $k_d$, the sound velocity $c_0$ inside the object 100, and the sound velocity $c_1$ inside the holding member 130.

The computation unit 152 may select an incidence angle $\theta_0$ and a refraction angle $\theta_d$ corresponding to the wave number $k_d$ from the memory unit 153 in which incidence angles $\theta_0$ and refraction angles $\theta_d$ corresponding to multiple wave numbers are stored. Alternatively, incidence angles $\theta_0$ and refraction angles $\theta_d$ corresponding to various sound velocities $c_0$ inside the object 100 and various sound velocities $c_1$ inside the holding member 130 may be stored in the memory unit 153. In this case, the computation unit 152 selects the corresponding incidence angle $\theta_0$ and the corresponding refraction angle $\theta_d$ on the basis of the sound velocity $c_0$ inside the object 100 and the sound velocity $c_1$ inside the holding member 130.

Subsequently, the computation unit 152 obtains, on the basis of the phase $\phi_d$ of the acoustic waves corresponding to the wave number $k_d$, the phase $\phi_0$ of the acoustic waves corresponding to the wave number $k_0$ in the case where the acoustic waves are not refracted. As illustrated in FIG. 4, each of the phase $\phi_d$ and the phase $\phi_0$ is a phase difference between the peak of the acoustic waves and the origin.

Now, the method for obtaining the phase $\phi_0$ is described.

The point at which the interface between the object 100 and the holding member 130 intersects the z axis is taken as an incident point I and the phases corresponding to the wave numbers $k_0$ and $k_d$ from the incident point I to the acoustic wave peaks are taken as $\phi_{0\_I}$ and $\phi_{d\_I}$, respectively. The phases $\phi_{0\_I}$ and $\phi_{d\_I}$ can be expressed by Expression 3 below from the geometrical relationship illustrated in FIG. 4.

$$\phi_{0\_I} = 2\pi|k_0|L\cos\theta_0 - \phi_0$$

$$\phi_{d\_I} = 2\pi|k_d|L\cos\theta_d - \phi_d \quad \text{(Expression 3)}$$

The wave front of the acoustic wave is continuous at the incident point I. Thus, the phases $\phi_{0\_I}$ and $\phi_{d\_I}$ from the incident point I to the acoustic wave peaks are the same and the following expression is satisfied.

$$2\pi|k_0|L\cos\theta_0 - \phi_0 = 2\pi|k_d|L\cos\theta_d - \phi_d \quad \text{(Expression 4)}$$

On the basis of Expression 4, the phase $\phi_0$, which is a component of the wave number $k_0$, is calculated as illustrated in Expression 5. Here, L denotes the thickness of the holding member 130 and $n = c_0/c_1$.

$$\begin{aligned}\phi_0 &= \phi_d + 2\pi|k_0|L\cos\theta_0 - 2\pi|k_d|L\cos\theta_d \\ &= \phi_d + 2\pi|k_0|L\cos\theta_0 - 2\pi n|k_0|L\cos\theta_d \\ &= \phi_d + 2\pi|k_0|L(\cos\theta_0 - n\cos\theta_d)\end{aligned} \quad \text{(Expression 5)}$$

Subsequently, as illustrated in Expression 7, the computation unit 152 calculates a complex value $K_d'$ by correcting the phase modulation using a phase difference $i\Delta\phi$ as a phase factor from the measured value $K_d$. Here, $\Delta\phi$ is a difference between the phases $\phi_0$ and $\phi_d$. The measured value $K_d$ is expressed by Expression 6, where A denotes the amplitude and $i\phi_d$ denotes the phase factor.

$$K_d = A \cdot e^{i\phi_d} \quad \text{(Expression 6)}$$

$$\begin{aligned}K_d' &= A \cdot e^{i\phi_0} \\ &= A \cdot e^{i[\phi_d + 2\pi|k_0|L(\cos\theta_0 - n\cos\theta_d)]} \\ &= K_d \cdot e^{i2\pi|k_0|L(\cos\theta_0 - n\cos\theta_d)} \\ &= K_d \cdot e^{i\Delta\phi}\end{aligned} \quad \text{(Expression 7)}$$

As will be understood from Expression 7, the complex value $K_d'$ in which the phase modulation corresponding to the wave number $k_d$ is corrected can be obtained by multiplying the measured value $K_d$ corresponding to the wave number $k_d$ by the complex number having the phase factor included in Expression 8. In Expression 8, $\text{sgn}(k_{0z})$ is a sign function that takes +1 when $k_{0z}$ is larger than or equal to zero and that takes −1 when $k_{0z}$ is negative. Thus far, the case where $k_{0z}$ is positive has been described. Also in the case where $k_{0z}$ is negative, it is found that Expression 8 when $\text{sgn}(k_{0z})$ is −1 serves as a phase factor as a result of the same procedure as that described above.

$$i\Delta\phi = \text{sgn}(k_{0z})i|k_0|L(\cos\theta_0 - n\cos\theta_d) \quad \text{(Expression 8)}$$

In the case where the sound velocity $c_0$ inside the object 100, the sound velocity $c_1$ inside the holding member 130, and the thickness L of the holding member 130 are found in advance, the phase factor illustrated in Expression 8 is uniquely determined as a result of determination of the target wave number $k_d$. In other words, the computation unit 152 can select the phase factor corresponding to any wave number $k_d$ from the memory unit 153 in which phase factors corresponding to multiple wave numbers have been stored in advance.

In this embodiment, the case where the peak of the amplitude of acoustic waves precedes the origin, that is, the case where the phases $\phi_0$ and $\phi_d$ are negative is described. However, Expression 7 and Expression 8 are applicable to cases no matter which sign $\phi_0$ and $\phi_d$ has.

Subsequently, the computation unit 152 can obtain the wave number spectrum K', in which phase modulation is corrected, as the second frequency signals by performing the above-described correction of phase modulation on measured values of corresponding wave numbers in the wave number spectrum K. Complex values corresponding to the wave numbers in the wave number spectrum K' in which the phase modulation is corrected are stored in the memory unit 153.

In this embodiment, the method for correcting the phase modulation attributable to the holding member 130 has been described. However, the phase modulation that can be corrected is not limited to the one attributable to the holding member 130. The correction of the phase modulation according to the embodiment is applicable to the case where the sound velocity distribution exists on the propagation path of the acoustic waves.

For example, the present invention is applicable to a phase modulation that occurs in the case where an interface exists inside the object 100 between structures in which sound travels at different velocities. In this case, structural information inside the object 100 has to be grasped before performing step S400 and the distribution of the sound velocity inside the object 100 has to be grasped from the structural information. To this end, a structural information obtaining unit such as a magnetic resonance imager (MRI), a diffusion optical tomographic apparatus, or an ultrasonic echo apparatus may obtain the structural information inside the object 100 before performing step S400. The structural information obtaining unit may be included in the object information obtaining system or provided as a separate unit. By applying the light source 110 according to the embodiment to a light source of a diffusion optical tomographic apparatus, the structural information inside the object 100 can be obtained while a size increase of the apparatus is minimized. In the case where the structural information inside the object 100 is presumable, the presumed structural information may be used. Alternatively, the signal processor 150 may obtain the sound velocity distribution on the basis of the structural information obtained in the above described manner.

The present invention is also applicable to a phase modulation attributable to a member disposed outside the object 100 other than the holding member 130.

Also in the case where there are three layers in which sound travels at different velocities, the phase modulation can be corrected by performing the same operations on the layers as those described above.

S500: Step of Obtaining Object Information on the Basis of Wave Number Spectrum in which Phase Modulation has been Corrected In this step, the computation unit 152 obtains object information on the basis of the corrected wave number spectrum obtained in step S400.

For example, as illustrated in Expression 9, the computation unit 152 performs the inverse Fourier transform on the wave number spectrum K' obtained in step S400 and in which the phase modulation has been corrected and thus obtains an initial acoustic pressure distribution $p_0$ (x, y, z) inside the object 100.

$$p_0(x,y,z) = F_{x,y,z}^{-1}(K') \quad \text{(Expression 9)}$$

The initial acoustic pressure distribution is obtained by using the complex value obtained by correcting the phase modulation attributable to the refraction at the holding member 130. Thus, the reduction of the quantitativeness due to the phase modulation is minimized.

The computation unit 152 may restore time-series detection signals, in which phase modulation is corrected, by performing operations in the order opposite to that of the operations illustrated in Expression 1 and Expression 2 on the wave number spectrum, in which phase modulation is corrected, obtained in step S400. In this case, the computation unit 152 can obtain an initial acoustic pressure distribution by performing appropriate reconstruction on the time-series detection signals, in which phase modulation is corrected. This method enables obtaining an initial acoustic pressure distribution with the performance of appropriate reconstruction instead of performing the inverse Fourier transform for reconstruction. Examples of appropriate reconstruction include a time-domain back projection method and a model based method.

Here, the computation unit 152 may obtain an absorption coefficient distribution inside the object 100 on the basis of the obtained initial acoustic pressure distribution and the distribution of light quantity of light projected on the object 100 inside the object 100. Alternatively, light beams having multiple different wavelengths may be individually subjected to steps S100 to S500, so that object information corresponding to the multiple wavelengths may be obtained. In addition, the concentration of materials inside the object may be obtained using the object information corresponding to the multiple wavelengths. Also in various types of object information thus obtained, a reduction of the quantitativeness due to the phase modulation is minimized.

S600: Step of Displaying Object Information

In this step, an image of the object information obtained in step S500 is displayed on the display unit 160. The computation unit 152 performs an operation such as luminance conversion on the object information obtained in step S500 in order that the object information can be displayed on the display unit 160, generates image data corresponding to the object information, and outputs the image data to the display unit 160. Since the object information displayed on the display unit 160 is information in which a reduction of the quantitativeness due to the phase modulation is minimized, the object information is suitably usable by practitioners such as medical doctors for diagnosis.

The above-described method for obtaining object information according to the embodiment enables obtaining object information in which the phase modulation of acoustic waves attributable to the sound velocity distribution of the holding member or the like is corrected. Thus, a reduction of the quantitativeness of the object information thus obtained can be minimized.

In this embodiment, correction of phase modulation performed by calculating a propagation path of one sound ray corresponding to a plane wave in accordance with the Snell's law can be performed by performing, on frequency signals, correction of phase modulation. In other words, compared to the method for correcting the phase modulation disclosed in Japanese Patent Laid-Open No. 2010-167258 in which the propagation paths of multiple sound rays of acoustic waves that have occurred as spherical waves are calculated in accordance with the Snell's law, the method for correcting the phase modulation according to the embodiment involves fewer calculations.

Second Embodiment

Figure 5:
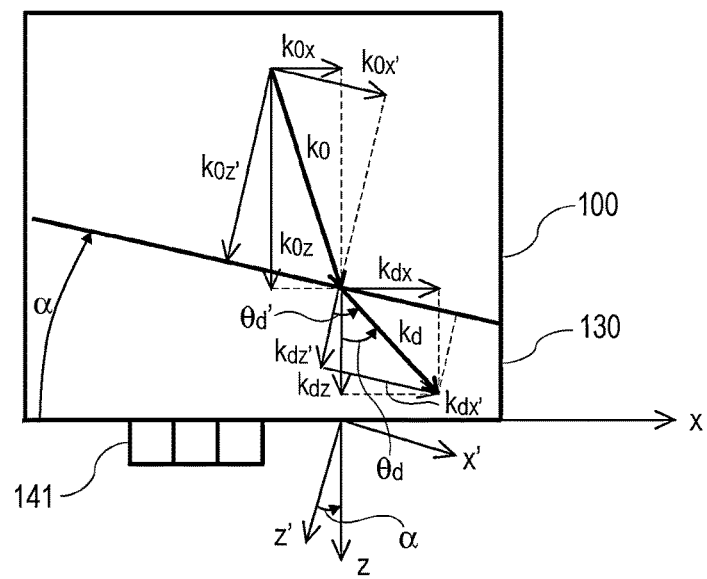
FIG. 5 illustrates correction of wave number modulation according to a second embodiment.

As illustrated in FIG. 5, the second embodiment describes the case where the interface between materials in which sound travels at different velocities is inclined at an angle α with respect to the acoustic-wave detection surface. In other words, the second embodiment describes the case where the detection surfaces of the multiple transducers 141 and the interface between the object 100 and the holding member 130 are disposed at an angle α around the y axis. In this embodiment, the angle α is an angle formed by the detection surfaces of the multiple transducers 141 and one surface of the holding member 130.

In front of or behind an interface between two layers in which the sound velocities are different, the wave number in the direction parallel to the interface is conserved. In other words, in the first embodiment, the wave numbers in the x and y axis directions of the wave number $k_0$ are respectively the same as the wave numbers in the x and y axis directions of the wave number $k_d$ since the interface between the object 100 and the holding member 130 is parallel to the acoustic-wave detection surface (x-y plane).

However, in the second embodiment, since the interface is rotated around the y axis, the wave number in the x axis direction in front of or behind the interface is not conserved. On the other hand, the wave number in the x' direction that is parallel to the interface is conserved. Thus, the wave number in the x axis direction of the wave number $k_0$ is different from the wave number in the x axis direction of the wave number $k_d$. In other words, if the correction of the phase modulation described in step S400 is performed assuming that the wave number in the x axis direction of acoustic waves before the acoustic waves propagate through the holding member 130 is $k_{dx}$, which is supposed to be $k_{0x}$, the effect of minimizing the reduction of the quantitativeness of the object information becomes insufficient.

In view of this, unlike in the first embodiment, in the second embodiment, correction of wave number modulation of acoustic waves attributable to the inclination of the interface between materials in which sound travels at different velocities is performed on the wave number spectrum before performing the correction of the phase modulation of acoustic waves.

Figure 6:
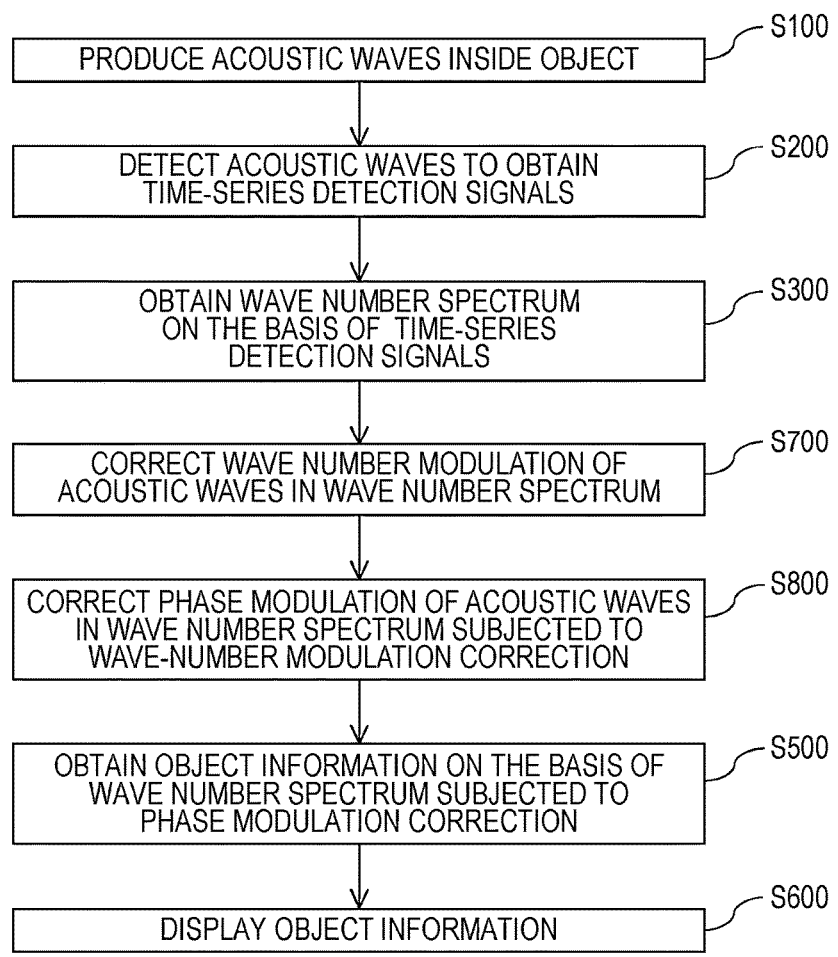
FIG. 6 is a flow chart of a method for obtaining object information according to the second embodiment.

Hereinbelow, the method for operating the object information obtaining system according to the embodiment is described along the flow chart in FIG. 6. The steps that are the same as those illustrated in FIG. 3 are denoted by the same reference symbols and are not described. Components that are the same as those described in the first embodiment are generally denoted by the same reference symbols and are not described.

S700: Step of Correcting Wave Number Modulation of Acoustic Waves in Wave Number Spectrum As described above, in this embodiment, the wave number in the x axis direction in front of or behind the interface is not conserved. On the other hand, the wave number of a component that is parallel to the interface (here, the x' axis direction) in front of or behind the interface is conserved. Here, the wave number in the y axis direction in front of or behind the interface is conserved.

In step S700, the wave number modulation is corrected as a result of the computation unit 152 associating the measured value $K_d$, corresponding to the wave number $k_d=(k_{dx}, k_{dy}, k_{dz})$ in the coordinate system (x, y, z) on the detection surface of the probe 140, to the wave number $k_0=(k_{0x}, k_{0y}, k_{0z})$ in the coordinate system of the detection surface. That is, the computation unit 152 obtains a third frequency signal in which wave number modulation is corrected.

For example, the computation unit 152 obtains the wave number $k_0$ ($k_{0x}$ and $k_{0z}$) from the wave number $k_d$ ($k_{dx}$ and $k_{dz}$) on the basis of Expression 10, which is derived from the affine transformation and the Snell's law.

$$\begin{bmatrix} k_{0x} \\ k_{0z} \end{bmatrix} = \begin{bmatrix} \cos^2\alpha + \sin^2\alpha \dfrac{\cos\theta_{d'}}{\sqrt{n^2 - \sin^2\theta_{d'}}} & \sin\alpha\cos\alpha\left(1 - \dfrac{\cos\theta_{d'}}{\sqrt{n^2 - \sin^2\theta_{d'}}}\right) \\ \sin\alpha\cos\alpha\left(1 - \dfrac{\cos\theta_{d'}}{\sqrt{n^2 - \sin^2\theta_{d'}}}\right) & \sin^2\alpha + \cos^2\alpha \dfrac{\cos\theta_{d'}}{\sqrt{n^2 - \sin^2\theta_{d'}}} \end{bmatrix} \begin{bmatrix} k_{dx} \\ k_{dz} \end{bmatrix}$$

(Expression 10)

The computation unit 152 then stores the measured value $K_d$, which has been stored in an address corresponding to the wave number $k_d$, in an address corresponding to the wave number $k_0$ calculated through Expression 10.

Here, $\theta_d'$ is calculated by adding the refraction angle $\theta_d$ and the angle $\alpha$. As described above, the refraction angle $\theta_d$ is uniquely determined from the wave number $k_d$. In other words, the computation unit 152 can calculate the wave number $k_0$ on the basis of information of the angle $\alpha$ formed by the detection surfaces of the multiple transducers 141 and the holding member 130. In the case where the angle $\alpha$ is not found in advance, the angle $\alpha$ may be obtained from images such as an image that can be taken by a measurement unit such as a charge coupled device (CCD).

The method for correcting the wave number modulation is not limited to the above method as long as the method enables obtaining the wave number $k_0$ in the coordinate system of the interface between materials in which sound travels at different velocities from the wave number $k_d$ in the coordinate system of the detection surface. For example, the computation unit 152 firstly obtains, through the affine transformation, the wave number $k_d$ in the coordinate system (x', y', z') at the interface between the object 100 and the holding member 130 from the wave number $k_d$ in the coordinate system on the detection surface and stores the wave number $k_d$ in the coordinate system (x', y', z') at the interface in the memory unit 153. Subsequently, the computation unit 152 obtains, through the Snell's law, the wave number $k_0$ in the coordinate system at the interface from the wave number $k_d$ in the coordinate system at the interface stored in the memory unit 153 and stores the wave number $k_0$ in the memory unit 153. Subsequently, the computation unit 152 obtains, through the affine transformation, the wave number $k_0$ in the coordinate system on the detection surface from the wave number $k_0$ in the coordinate system at the interface stored in the memory unit 153 and stores the wave number $k_0$ in the coordinate system on the detection surface in the memory unit 153. The wave number $k_0$ in the coordinate system on the detection surface may be obtained from the wave number $k_d$ in the coordinate system on the detection surface in this manner.

In this step, the wave number spectrum in which the wave number modulation has been corrected can be obtained by performing the above-described processing on each wave number in the wave number spectrum.

In the case where an address in which the measured value $K_d$ is to be stored is obtained before the measured value $K_d$ is stored, the measured value $K_d$ may be obtained from the multiple time-series detection signals stored in the memory unit 153 and may be directly stored to the address corresponding to the wave number $k_0$.

In this step, correction of phase modulation may be performed using the measured value $K_d$ as a measured value corresponding to the wave number $k_0$ in step S800, described below, without obtaining the wave number spectrum, in which wave number modulation is corrected. In this embodiment, such a case can be also regarded as the case involving the correction of the wave number modulation.

As in the case of the first embodiment, correctable wave number modulation is not limited to the one attributable to the inclination of the holding member 130 in this embodiment. The correction of the wave number modulation according to the embodiment is applicable to the case where an interface between two layers in which sound travels at different velocities is disposed at a certain angle with the acoustic-wave detection surface in the propagation path of the acoustic waves. Moreover, even in the case where there are three layers in which sound travels at different sound velocities, the wave number modulation can be corrected by performing the same processing on each layer.

This embodiment describes the case where there is no inclination in the y axis direction. In the case there is an inclination in the y axis direction, the wave number modulation can be easily corrected by extending Expression 10, which is a two-dimensional affine transformation, to a typical three-dimensional affine transformation.

In this embodiment, the affine transformation is used for transformation of the coordinate system but another rotational transform may also be used. For example, Euler transform or other types of transformation may be used.

S800: Step of Correcting Phase Modulation of Acoustic Waves in Wave Number Spectrum, in which Wave Number Modulation is Corrected In step S800, correction of phase modulation is performed on the wave number spectrum obtained in step S700 and in which the wave number modulation has been corrected. Step S800 corresponds to step S400 according to the first embodiment. Also in step S800, performing the same correction as that performed in step S400 enables the correction of the wave number modulation and the phase modulation of acoustic waves attributable to the interface between two layers in which sound travels at different velocities. Thus, the quantitativeness of object information obtainable in the subsequent step of Step S500 can be improved.

As described above, correction of phase modulation may be performed using, for example, the measured value $K_d$ corresponding to the wave number $k_d$ obtained in step S300 as a measured value corresponding to the wave number $k_0$. This method also enables the correction of the wave number modulation and the phase modulation of acoustic waves attributable to the interface between two layers in which sound travels at different velocities.

As described above, the method for obtaining object information according to the embodiment enables obtaining object information in which wave number modulation has been corrected in addition to the phase modulation of acoustic waves attributable to the sound velocity distribution in the holding member or the like. Thus, a reduction of an obtainable quantitativeness of object information can be minimized.

EXAMPLES

Hereinbelow, results of simulation of performing the method for obtaining object information according to the first or second embodiment are described.

In the following description, a physical quantity not affixed with a unit represents that the physical quantity is standardized with an appropriate constant. In the following description, the origin of coordinates is defined at one vertex of a calculation space and each side of the calculation space has a coordinate extending from zero to a positive maximum value.

In this example, the following four pieces of measurement data (multiple time-series signals) are calculated through the simulation.

Firstly, first measurement data pieces are calculated in the following manner. The calculation space is a three-dimensional space having a width (x) of 120 mm, a length (y) of 46 mm, and a height (z) of 60 mm. The three-dimensional space was divided into cubic cells each having sides of 0.5 mm. Nine wire-shaped digital phantoms having a diameter of 1 mm, a length of 46 mm, and a fixed inner pressure of 1 are disposed in the calculation space at intervals of 5 mm in width and at intervals of 5 mm in height. As a result of convolution of an initial pressure distribution inside the calculation space thus obtained and outward spherical waves, which are fundamental solutions of a wave equation in a free space, a pressure distribution at arbitrary time was obtained. However, at the interface between regions having different acoustic characteristics, the outward spherical waves were refracted in accordance with the Snell's law. The acoustic characteristics inside the calculation space were divided into two regions by one interface parallel to the z axis. The position at the division was z=10 mm and the divided regions were referred to as a first region and a second region in descending order of the z coordinate. The acoustic characteristics in each region were defined as follows. The first region had a density of 1 and a modulus of elasticity of 1 and the second region had a density of 0.833 and a modulus of elasticity of 1.8. The bottom surface of the calculation space (z=0 mm) was regarded as a detection surface of the probe and was divided into square cells each having sides of 2 mm. An averaged pressure distribution in each cell was chronologically recorded and the obtained results were first measurement data pieces.

Second measurement data pieces are calculated in the following manner. The calculation space is a two-dimensional space having a width (x) of 30 mm and a length (y) of 60 mm. The two-dimensional space was divided into square cells each having sides of 50 μm. One Gaussian distribution digital phantom having a maximum pressure of 1 and a standard deviation of 0.5 mm is disposed at a position (x=15 mm, y=15 mm) of the calculation space. The pressure distribution at arbitrary time was calculated by the general acoustic finite-difference time domain (FDTD) method using an initial pressure distribution inside the calculation space obtained in the above-described method as an initial value. The acoustic characteristics inside the calculation space were divided into three regions by two interfaces parallel to the x axis. The positions at the division were y=30 mm and y=40 mm and the divided regions were referred to as a first region, a second region, and a third region in ascending order of the y coordinate. The acoustic characteristics in each region were defined as follows. The first region had a density of 1 and a modulus of elasticity of 1, the second region had a density of 0.833 and a modulus of elasticity of 1.8, and the third region had a density of 0.91 and a modulus of elasticity of 0.9. A straight line parallel to the x axis and having a length of 27 mm was drawn inside the calculation space (y=50 mm) and regarded as a detection surface of the probe. The line was divided into sections each having a length of 45 μm. The pressure distribution evaluated at the center of each section was chronologically recorded and the obtained results were second measurement data pieces.

Third measurement data pieces are calculated in the following manner. All the conditions were the same as those set to obtain the second measurement data pieces except for the probe. A straight line that has a length of 27 mm, that forms an angle of 15 degrees with respect to the x axis, and that passes through the point where x=15 mm and y=50 mm was drawn inside the calculation space and regarded as a detection surface of the probe. The line was divided into sections each having a length of 45 μm. The pressure distribution evaluated at the center of each section was chronologically recorded and the obtained results were third measurement data pieces. The third measurement data pieces are different from the second measurement data pieces in terms that the interferences that separate regions having different acoustic characteristics from each other are not parallel to the detection surface.

Fourth measurement data pieces are calculated in the following manner. All the conditions were the same as those set to obtain the second measurement data pieces except for the distribution of the acoustic characteristics. The acoustic characteristics inside the calculation space were divided into three regions by two arcs, serving as interfaces, which have different radii and are concentric with each other at the point where x=15 mm and y=−70 mm. The first arc had a diameter of 100 mm and the second arc had a diameter of 110 mm. The divided regions were referred to as the same names as those in the case of the second measurement data pieces and the acoustic characteristics in each region were defined in the same manner as in the case of the second measurement data pieces. By providing a detection surface in the similar manner as in the case of the second measurement data pieces, the pressure distribution was chronologically recorded and the obtained results were used as fourth measurement data pieces. The fourth measurement data pieces are different from the second measurement data pieces in terms that the interfaces that separate regions having different acoustic characteristics from each other are arcs having large radii of curvature.

In the case of the first and second measurement data pieces, the detection surface is parallel to the interfaces between regions in which sound travels at different velocities. Thus, the correction of the wave number modulation described in the second embodiment is not performed.

All the calculations of the propagation path of plane waves in the Fourier transform were performed using the Snell's law. Specifically, assuming that the Snell's law is satisfied at each interface, an angle of emergence was calculated using a known incidence angle. This calculation was sequentially repeated and the wave number of plane waves in each region was obtained. Then, propagation time of the plane waves was calculated on the basis of the geometric length of the propagation path thus obtained and the sound velocity in each region.

Figure 7:
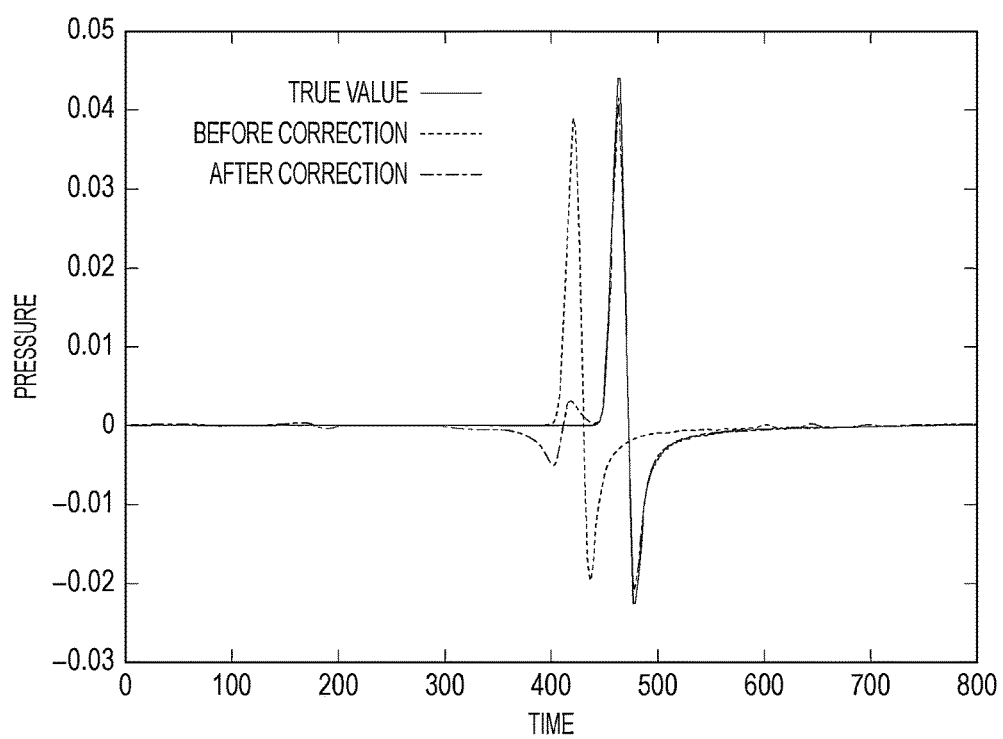
FIG. 7 illustrates results of the correction of the phase modulation according to examples.

FIG. 7 illustrates signals obtained after performing correction of phase modulation on the second measurement data pieces (signals after correction), the second measurement data pieces (signals before correction), and signals obtained in the case where the sound velocity is uniform (true value signals).

Here, the signals after the correction of the phase modulation are time-series signals of actual time obtained by performing the inverse Fourier transform on the wave number spectrum, the correction of the phase modulation being performed on the second measurement data pieces in the wave number spectrum and the wave number spectrum being obtained by performing steps S300 and S400 according to the first embodiment. Here, these signals represent values measured at the center of the probe. In FIG. 7, the vertical axis represents the pressure and the horizontal axis represents the standardized time.

As found from FIG. 7, the signals after the correction of the phase modulation were closer to the true value signals than the signals before the correction.

Figure 8A:
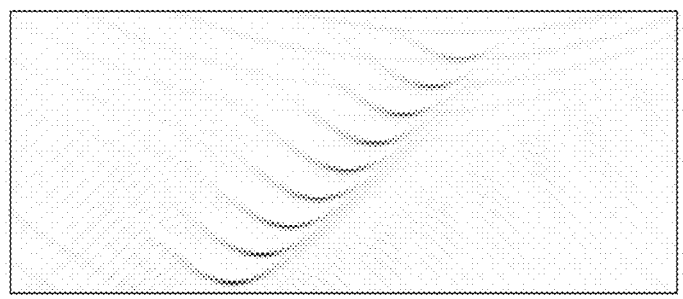
FIGS. 8A and 8B illustrate other results of the correction of the phase modulation according to examples.
Figure 8B:
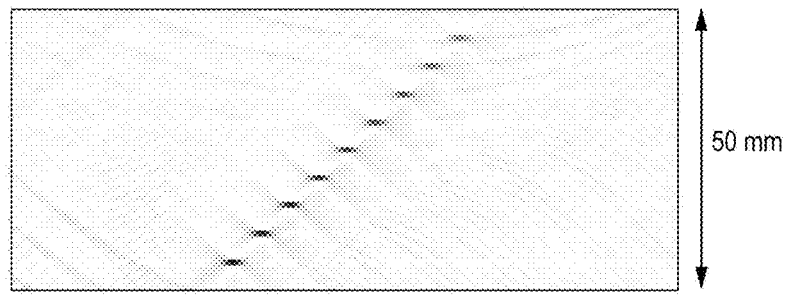
Figure 8B:
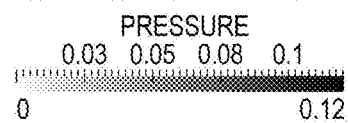

FIG. 8A illustrates an initial acoustic pressure distribution reconstructed without performing correction of phase modulation on the first measurement data pieces and FIG. 8B illustrates an initial acoustic pressure distribution reconstructed after performing correction of phase modulation on the first measurement data pieces. Specifically, FIG. 8B illustrates results obtained by reconstructing, through the k-space method, the wave number spectrum obtained by performing steps S300 and S400 according to the first embodiment and in which correction of phase modulation is performed on the first measurement data pieces, the k-space method being exemplified in Journal of Biomedical Optics 15 (2), 021314 (March/April 2010)).

As illustrated in FIG. 8A, before the correction, the cross-sectional shape of the wires was warped into a bow, which is different from the original shape, and the wires were displaced and had low contrasts. After the correction, on the other hand, as illustrated in FIG. 8B, the cross-sectional shape of the wires was restored and the wires were returned to the original positions and had higher contrasts.

The time taken to calculate the distribution illustrated in FIG. 8B was 3.7 seconds including the time required for performing the reconstruction using the k-space method and the time required for inputting and outputting data under the environment of the calculator of 1.4 GFLOPS. On the other hands, the time taken to perform the reconstruction using the k-space method without performing the correction was 3.1 seconds. In other words, the difference resulting from subtraction, 0.6 seconds, was the time taken to perform the correction of the phase modulation.

On the other hands, when time taken to perform the method described in Japanese Patent Laid-Open No. 2010-167258 was similarly measured, performing the operation including the correction took 877 seconds and performing the operation without the correction took 137 seconds. Thus, the difference resulting from subtraction, 740 seconds, was the time taken to perform the correction of the phase modulation. Here, since the back projection method is the only reconstruction method feasible in the method described in Japanese Patent Laid-Open No. 2010-167258, the back projection method was used as the reconstruction method in this measurement.

These results show that the correction method according to the embodiment enables reduction of time taken for the correction of the phase modulation compared to the correction method according to an existing technology. In other words, the correction method according to the embodiment involves fewer calculations than in the case of the existing correction method.

FIGS. 9A to 9G illustrate results of reconstruction after performing the correction of the phase modulation on the second measurement data pieces and performing the correction of the phase modulation and the correction of the wave number modulation on the third and fourth measurement data pieces. Here, in order to clarify that the method according to the embodiment is applicable to the reconstruction method other than the k-space method, the reconstruction in the calculation illustrated in FIG. 9 was performed by the back projection method.

FIGS. 9A, 9B, and 9C on the upper part illustrate the results of reconstruction of the second, third, and fourth measurement data pieces without the correction. FIGS. 9D, 9E, and 9F on the lower part illustrate the results of reconstruction of the second, third, and fourth measurement data pieces after the correction. For the reference purpose, FIG. 9G on the lower part illustrates the result of reconstruction in the case where the sound velocity is uniform (while the conditions of the probe are similar to the case of the second measurement data pieces).

As found from the images illustrated in FIGS. 9A to 9G, the reduction of the quantitativeness of the object information was successfully minimized by the correction in the case where there were three or more regions in which sound travels at different velocities, in the case where the interfaces were not parallel to the detection surface, and in the case where the interfaces were curved surfaces having a large radius of curvature.

The examples show that the method for obtaining object information according to the present invention enables obtaining object information in which, not only phase modulation of acoustic waves attributable to the sound velocity distribution, but also the wave number modulation is corrected. The examples also show that the correction can be performed with fewer calculations than in the case of an existing method.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-133533, filed Jun. 26, 2013 which is hereby incorporated by reference herein in its entirety.

What is claimed is:

1. An object information obtaining system, comprising:
a holding member configured to hold an object;
a probe configured to output a plurality of detection signals in time-domain by detecting acoustic waves at a plurality of positions, the acoustic waves having occurred inside the object and having propagated through the holding member; and
a signal processor configured to:
obtain a first frequency signal as a first set of complex numbers corresponding to wave numbers of the acoustic waves on the basis of the plurality of detection signals in time-domain,
obtain a second frequency signal as a second set of complex numbers by performing, on the first frequency signal as the first complex numbers, correction of phase modulation of the acoustic waves caused by refraction of the acoustic waves due to the holding member, and
obtain object information inside the object by performing a reconstruction on basis of the second frequency signal,
wherein the signal processor is configured to perform the correction of the phase modulation by changing a phase corresponding to the first frequency signal as the first set,
wherein the signal processor is configured to obtain a first complex number representing the correction of the phase modulation based on first and second phase values corresponding to first and second wave numbers, respectively,
wherein the first phase value is equal to sum of the second phase value and a phase difference,
wherein the phase difference is a product of a thickness of the holding member, an absolute value of the first wave number, and a difference between a cosine of an incidence angle and a cosine of a refraction angle scaled by a ratio between sound velocities inside the object and inside the holding member,
wherein the incidence and refraction angles are related according to Snell's law,
wherein the first complex number is equal to a product of a measured wave number corresponding to the second wave number and a second complex number having the phase difference as a phase factor,
wherein the measured wave number is equal to a product of an amplitude and a third complex number having the second phase value as a phase factor,
wherein the phase difference has a sign according to whether a component of the first wave number is non-negative or negative, and
wherein the signal processor is configured to multiply the first frequency signal as the first set by the first complex number to obtain the second frequency signal as the second set.

2. The object information obtaining system according to claim 1,
wherein the signal processor includes a memory unit in which a plurality of phase factors is stored, and
wherein the phase factor representing the phase modulation is selected from the memory unit.

3. The object information obtaining system according to claim 1,
wherein the signal processor is configured to obtain a third frequency signal as third complex numbers by performing, on the second frequency signal as the second complex numbers, correction of wave number modulation of the acoustic waves caused by refraction of the acoustic waves due to the holding member, and
wherein the signal processor is configured to obtain the object information by performing the reconstruction on the basis of the third frequency signal.

4. The object information obtaining system according to claim 3, wherein the signal processor is configured to perform the correction of the wave number modulation on the basis of an angle formed between a detection surface of the probe and an interface between the holding member and the object.

5. An object information obtaining system, comprising a signal processor configured to:
obtain a first frequency signal as a first set of complex numbers corresponding to wave numbers of the acoustic waves on basis of a plurality of detection signals in time-domain which is obtained by detecting acoustic waves at a plurality of positions, the acoustic waves having occurred inside an object,
obtain a second frequency signal as a second set of complex numbers by performing, on the first frequency signal as the first complex numbers, correction of phase modulation of the acoustic waves caused by refraction of the acoustic waves due to a sound velocity distribution in a propagation path of the acoustic waves, and
obtain object information inside the object by performing a reconstruction on the basis of the second frequency signal,
wherein the signal processor is configured to perform the correction of the phase modulation by changing a phase corresponding to the first frequency signal as the first set,
wherein the signal processor is configured to obtain a first complex number representing the correction of the phase modulation based on first and second phase values corresponding to first and second wave numbers, respectively,
wherein the first phase value is equal to sum of the second phase value and a phase difference,
wherein the phase difference is a product of a thickness of the holding member, an absolute value of the first wave number, and a difference between a cosine of an incidence angle and a cosine of a refraction angle scaled by a ratio between sound velocities inside regions having different acoustic characteristics in the object, wherein the incidence and refraction angles are related according to Snell's law, wherein the first complex number is equal to a product of a measured wave number corresponding to the second wave number and a second complex number having the phase difference as a phase factor, wherein the measured wave number is equal to a product of an amplitude and a third complex number having the second phase value as a phase factor, wherein the phase difference has a sign according to whether a component of the first wave number is non-negative or negative, and wherein the signal processor is configured to multiply the first frequency signal as the first set by the first complex number to obtain the second frequency signal as the second set.

6. The object information obtaining system according to claim 5, wherein the signal processor is configured to obtain a third frequency signal as third complex numbers by performing, on the second frequency signal as the second complex numbers, correction of wave number modulation of the acoustic waves due to the sound velocity distribution, and wherein the signal processor is configured to obtain the object information by performing the reconstruction on the basis of the third frequency signal.

7. The object information obtaining system according to claim 5, wherein the signal processor is configured to obtain the sound velocity distribution on the basis of structural information inside the object.

8. The object information obtaining system according to claim 1, wherein the signal processor is configured to obtain the first frequency signal by performing Fourier transform on the plurality of detection signals in time-domain, in a time direction and a spatial direction.

9. The object information obtaining system according to claim 1, wherein the signal processor is configured to obtain a plurality of detection signals in time-domain, in which the phase modulation is corrected, by performing inverse Fourier transform on the second frequency signal, and wherein the signal processor is configured to obtain the object information by performing the reconstruction on the basis of the plurality of detection signals in time-domain.

10. An object information obtaining system, comprising a signal processor configured to:

obtain a first frequency signal as a first set of complex numbers corresponding to wave numbers of the acoustic waves on basis of a plurality of detection signals in time-domain which is obtained by detecting acoustic waves at a plurality of positions, the acoustic waves having occurred inside an object, obtain a second frequency signal as a second set of complex numbers by performing, on the first frequency signal as the first set, correction of wave number modulation of the acoustic waves caused by refraction of the acoustic waves due to a sound velocity distribution in a propagation path of the acoustic waves, and obtain object information inside the object by performing a reconstruction on the basis of the second frequency signal, wherein the signal processor is configured to perform the correction of the wave number modulation by changing a wave number corresponding to the first frequency signal as the first set, wherein the signal processor is configured to obtain a first complex number representing the correction of the wave number modulation based on first and second phase values corresponding to first and second wave numbers, respectively, wherein the first phase value is equal to sum of the second phase value and a phase difference, wherein the phase difference is a product of a thickness of the holding member, an absolute value of the first wave number, and a difference between a cosine of an incidence angle and a cosine of a refraction angle scaled by a ratio between sound velocities inside the object and inside the holding member, wherein the incidence and refraction angles are related according to Snell's law, wherein the first complex number is equal to a product of a measured wave number corresponding to the second wave number and a second complex number having the phase difference as a phase factor, wherein the measured wave number is equal to a product of an amplitude and a third complex number having the second phase value as a phase factor, wherein the phase difference has a sign according to whether a component of the first wave number is non-negative or negative, and wherein the signal processor is configured to multiply the first frequency signal as the first set by the first complex number to obtain the second frequency signal as the second set.

11. A method for processing a signal to obtain object information inside an object on the basis of a plurality of detection signals in time-domain obtained by detecting acoustic waves, which have occurred inside the object, at a plurality of positions, the method comprising the steps of:

obtaining a first frequency signal as a first set of complex numbers corresponding to wave numbers of the acoustic waves on the basis of the plurality of detection signals in time-domain;

obtaining a second frequency signal as a second set of complex numbers by performing, on the first frequency signal as the first set, correction of phase modulation or wave number modulation of the acoustic waves caused by refraction of the acoustic waves due to a sound velocity distribution in a propagation path of the acoustic waves; and obtaining object information inside the object by performing a reconstruction on the basis of the second frequency signal, wherein the correction of the phase modulation is performed by changing a phase corresponding to the first frequency signal as the first set, wherein the obtaining the second frequency signal includes:

obtaining a first complex number representing the correction of the phase modulation based on first and second phase values corresponding to first and second wave numbers, respectively, wherein the first phase value is equal to sum of the second phase value and a phase difference, wherein the phase difference is a product of a thickness of the holding member, an absolute value of the first wave number, and a difference between a cosine of an incidence angle and a cosine of a refraction angle scaled by a ratio between sound velocities inside regions having different acoustic characteristics in the object, wherein the incidence and refraction angles are related according to Snell's law, wherein the first complex number is equal to a product of a measured wave number corresponding to the second wave number and a second complex number having the phase difference as a phase factor, wherein the measured wave number is equal to a product of an amplitude and a third complex number having the second phase value as a phase factor, wherein the phase difference has a sign according to whether a component of the first wave number is non-negative or negative, and multiplying the first frequency signal as the first set by the first complex number to obtain the second frequency signal as the second set.

12. A non-transitory storage medium in which a program that causes a computer to execute the signal processing method according to claim 11 is stored.

13. The object information obtaining system according to claim 5, further comprising, a probe configured to output the plurality of detection signals in time-domain by detecting the acoustic waves at the plurality of positions.

14. The object information obtaining system according to claim 10, further comprising, a probe configured to output the plurality of detection signals in time-domain by detecting the acoustic waves at the plurality of positions.

15. The object information obtaining system according to claim 1, wherein the signal processor is configured to multiply the first frequency signal as the first set by the first complex number according to following formulas:

$$\phi_0 = \phi_d + |k_0| L(\cos \theta_0 - n \cos \theta_d) \quad (1)$$

$$K_d = A \cdot e^{i\phi_d} \quad (2)$$

$$K'_d = K_d \cdot e^{i\Delta\phi} \quad (3)$$

$$i\Delta\phi = sgn(k_{0z}) i |k_0| L(\cos \theta_0 - n \cos \theta_d) \quad (4)$$

wherein $\phi_0$ and $\phi_d$ are the first and second phase values corresponding respectively to the first and second wave numbers, $k_0$ is the first wave number, L is the thickness of the holding member, $\theta_0$ is the incidence angle, $\theta_d$ is the refraction angle, n is the ratio between the sound velocities, $K'_d$ is the first complex number, $K_d$ is the measured wave number corresponding to the second wave number, $e^{i\Delta\phi}$ is the second complex number, $\Delta\phi$ is the phase difference, A is the amplitude, $e^{i\phi_d}$ is the third complex number, and $k_{0z}$ is the component of the first wave number.

16. The object information obtaining system according to claim 5, wherein the signal processor is configured to multiply the first frequency signal as the first set by the first complex number according to following formulas:

$$\phi_0 = \phi_d + |k_0| L(\cos \theta_0 - n \cos \theta_d) \quad (1)$$

$$K_d = A \cdot e^{i\phi_d} \quad (2)$$

$$K'_d = K_d \cdot e^{i\Delta\phi} \quad (3)$$

$$i\Delta\phi = sgn(k_{0z}) i |k_0| L(\cos \theta_0 - n \cos \theta_d) \quad (4)$$

wherein $\phi_0$ and $\phi_d$ are the first and second phase values corresponding respectively to the first and second wave numbers, $k_0$ is the first wave number, L is the thickness of the holding member, $\theta_0$ is the incidence angle, $\theta_d$ is the refraction angle, n is the ratio between the sound velocities, $K'_d$ is the first complex number, $K_d$ is the measured wave number corresponding to the second wave number, $e^{i\Delta\phi}$ is the second complex number, $\Delta\phi$ is the phase difference, A is the amplitude, $e^{i\phi_d}$ is the third complex number, and $k_{0z}$ is the component of the first wave number.

17. The method according to claim 11, wherein the obtaining the second frequency signal as the second set includes multiplying the first frequency signal as the first set by the first complex number according to following formulas:

$$\phi_0 = \phi_d + |k_0| L(\cos \theta_0 - n \cos \theta_d) \quad (1)$$

$$K_d = A \cdot e^{i\phi_d} \quad (2)$$

$$K'_d = K_d \cdot e^{i\Delta\phi} \quad (3)$$

$$i\Delta\phi = sgn(k_{0z}) i |k_0| L(\cos \theta_0 - n \cos \theta_d) \quad (4)$$

wherein $\phi_0$ and $\phi_d$ are the first and second phase values corresponding respectively to the first and second wave numbers, $k_0$ is the first wave number, L is the thickness of the holding member, $\theta_0$ the incidence angle, $\theta_d$ is the refraction angle, n is the ratio between the sound velocities, $K'_d$ is the first complex number, $K_d$ is the measured wave number corresponding to the second wave number, $e^{i\Delta\phi}$ is the second complex number, $\Delta\phi$ is the phase difference, A is the amplitude, $e^{i\phi_d}$ is the third complex number, and $k_{0z}$ is the component of the first wave number.

18. The object information obtaining system according to claim 4, wherein the signal processor is configured to perform the correction of the wave number modulation by storing the second frequency signal in an address of wave number corresponding to the angle, the second frequency signal stored in the address indicating the third frequency signal.

19. The object information obtaining system according to claim 3, wherein a detection surface of the probe and an interface between the holding member and the object is not parallel.

20. The object information obtaining system according to claim 6, wherein the signal processor is configured to perform the correction of the wave number modulation on the basis of an angle formed between a detection surface of the probe and an interface between regions having different acoustic characteristics in the object.

21. The object information obtaining system according to claim 20, wherein the signal processor is configured to perform the correction of the wave number modulation by storing the second frequency signal in an address of wave number corresponding to the angle, the second frequency signal stored in the address indicating the third frequency signal.

22. The object information obtaining system according to claim 6, wherein a detection surface of the probe and an interface between the regions having different acoustic characteristics in the object are not parallel.

23. The object information obtaining system according to claim 10, wherein the signal processor is configured to perform the correction of the wave number modulation on the basis of an angle formed between a detection surface of the probe and an interface between the regions having different acoustic characteristics in the object.

24. The object information obtaining system according to claim 23, wherein the signal processor is configured to perform the correction of the wave number modulation by storing the second frequency signal in an address of wave number corresponding to the angle, the second frequency signal stored in the address indicating the third frequency signal.

25. The object information obtaining system according to claim 10, wherein a detection surface of the probe and an interface between regions having different acoustic characteristics in the object are not parallel.

26. The method according to claim 11, wherein the obtaining object information includes:
 obtaining a third frequency signal as third complex numbers by performing, on the second frequency signal as the second complex numbers, correction of wave number modulation of the acoustic waves caused by refraction of the acoustic waves due to the sound velocity distribution, and
 obtaining the object information by performing the reconstruction on the basis of the third frequency signal.

27. The method according to claim 26, wherein the correction of the wave number modulation is performed on the basis of an angle formed between a detection surface of the probe and an interface between regions having different acoustic characteristics in the object.

28. The method according to claim 27, wherein the correction of the wave number modulation is performed by storing the second frequency signal in an address of wave number corresponding to the angle, the second frequency signal stored in the address indicating the third frequency signal.

29. The method according to claim 26, wherein a detection surface of the probe and an interface between regions having different acoustic characteristics in the object are not parallel.

30. The object information obtaining system according to claim 10, wherein the signal processor is configured to multiply the first frequency signal as the first set by the first complex number according to following formulas:

$$\phi_0 = \phi_d + |k_0| L (\cos\theta_0 - n\cos\theta_d) \quad (1)$$

$$K_d = A \cdot e^{i\phi_d} \quad (2)$$

$$K'_d = K_d \cdot e^{i\Delta\phi} \quad (3)$$

$$i\Delta\phi = sgn(k_{0z}) i |k_0| L (\cos\theta_0 - n\cos\theta_d) \quad (4)$$

wherein $\phi_0$ and $\phi_d$ are the first and second phase values corresponding respectively to the first and second wave numbers, $k_0$ is the first wave number, L is the thickness of the holding member, $\theta_0$ the incidence angle, $\theta_d$ is the refraction angle, n is the ratio between the sound velocities, $K'_d$ is the first complex number, $K_d$ is the measured wave number corresponding to the second wave number, $e^{i\Delta\phi}$ is the second complex number, $\Delta\phi$ is the phase difference, A is the amplitude, $e^{i\phi_d}$ is the third complex number, and $k_{0z}$ is the component of the first wave number.

* * * * *